(12) United States Patent
Choi et al.

(10) Patent No.: US 8,871,067 B2
(45) Date of Patent: Oct. 28, 2014

(54) SENSOR FOR DETECTING HYDROGEN PEROXIDE

(71) Applicant: Industry-University Cooperation Foundation Sogang University, Seoul (KR)

(72) Inventors: Jeong Woo Choi, Seoul (KR); Ajay Kumar Yagati, Seoul (KR); Taek Lee, Seoul (KR); Jun Hong Min, Seongnam-Si (KR)

(73) Assignee: Industry-University Cooperation Foundation Sogang University, Seoul (KR)

( * ) Notice: Subject to any disclaimer, the term of this patent is extended or adjusted under 35 U.S.C. 154(b) by 0 days.

(21) Appl. No.: 13/673,710

(22) Filed: Nov. 9, 2012

(65) Prior Publication Data

US 2013/0233729 A1 Sep. 12, 2013

(30) Foreign Application Priority Data

Mar. 6, 2012 (KR) .......................... 10-2012-0022832

(51) Int. Cl.
*G01N 27/30* (2006.01)
*G01N 27/12* (2006.01)
*G01N 27/403* (2006.01)
*C07K 17/14* (2006.01)

(52) U.S. Cl.
CPC ............ *G01N 27/403* (2013.01); *G01N 27/127* (2013.01); *C07K 17/14* (2013.01)
USPC ........................................................ 204/400

(58) Field of Classification Search
USPC ...................... 204/400, 403.01; 205/782, 775
See application file for complete search history.

(56) References Cited

PUBLICATIONS

Liu et al., "Optical Sensing of Electrochemical Reactions on a Bio Hybrid Nanoparticle," Nanobiophotonics and Biomedical Applications II, edited by Alexander N. Cartwright., Marek Osinski, Proceedings of SPIE vol. 5705 (SPIE, Bellingham, WA 2005)pp. 123-130.*
Dutta-Gupta et al., "Ultrasensitive system for the real time detection of H2O2 based on strong coupling in a bio-plasmonic system," Plasmonics in Biology and Medicine IX, edited by Tuan Vo-Dinh, Joseph R. Lakowicz, Proc. of SPIE vol. 8234, 82340K (pp. 82340K-1 to 82340K-6), 2012 SPIE, which was published on Feb. 16, 2012.*
Brown et al., "Morphology-Dependent Electrochemistry of Cytochrome c at Au Colloid-Modified $SnO_2$ Electrodes," J. Am. Chem. Soc. 118: 1154-1157, 1996.
Ju et al., "Electrochemistry of Cytochrome c Immobilized on Colloidal Gold Modified Carbon Paste Electrodes and Its Electrocatalytic Activity," Electroanalysis 14, No. 2: 141-147, 2002.
Lian et al., "A Hydrogen Peroxide Sensor Based on Electrochemically Roughened Silver Electrodes," Electrochimica Acta 54: 4334-4339, 2009.

(Continued)

*Primary Examiner* — Alex Noguerola
(74) *Attorney, Agent, or Firm* — Clark & Elbing LLP (57) ABSTRACT

The present invention relates to a sensor for detecting hydrogen peroxide, comprising: (a) a gold (Au) nanoparticle conjugated with a conducting oxide substrate comprising a conduction oxide; (b) a cytochrome c immobilized on the gold nanoparticle. In the performance of the present sensor, current values are increased in parallel with increased hydrogen peroxide concentration. Such performance enables to easily analyze the presence or concentration of hydrogen peroxide.

6 Claims, 9 Drawing Sheets

(56) References Cited

PUBLICATIONS

Yagati et al., "Amperometric Sensor for Hydrogen Peroxide Based on Direct Electron Transfer of *Spinach* Ferredoxin on Au Electrode," Bioelectrochemistry, 2010.

Yagati et al., "Nanoscale Biomemory Device Composed of Recombinant Azurin on Hexagonal Au Nanopattern," IEEE-Nanomed 2011 jointly organized with Biotronics 2011, 2011.

Yagati et al., "Electrochemical Performance of Gold Nanoparticle-Cytochrome C Hybrid Interface for $H_2O_2$ Detection," Biointerfaces 92: 161-167, 2012.

* cited by examiner

Mean roughness (Ra); RMS (Rq); Max. height (Rmax); 10 pt. mean (Rz); Peak threshold; Max. peak height (Rp); Avg. max. height (Rpm); Max. depth (Rvm); Area thresh abs.

Fig. 7c ical field. As a result, the present inventors have found that where hydrogen

SENSOR FOR DETECTING HYDROGEN PEROXIDE

CROSS-REFERENCE TO RELATED APPLICATIONS

This application claims priority from Korean Patent Application No. 2012-0022832, filed on Mar. 6, 2012, in the Korean Intellectual Property Office, the disclosure of which is incorporated herein by reference.

BACKGROUND OF THE INVENTION

1. Field of the Invention

The present invention relates to a sensor for detecting hydrogen peroxide.

2. Description of the Related Art

The detection of hydrogen peroxide ($H_2O_2$) is important to many fields including industry, clinical control and environmental protection [1,2]. Many analytical methods have been developed for this purpose but amperometric enzyme-based biosensors have received considerable attention due to its convenience, high sensitivity and selectivity [3,4]. However, a significant challenge in the development of sensitive and stable sensors is the effective immobilization of enzyme and/or any nanostructured materials (such as carbon nanotubes, quantum dots, nanoparticles, etc.) to solid electrode surfaces [5]. Electrochemical biosensors for detection of $H_2O_2$ are mostly designed based on immobilization of horseradish peroxidase (HRP) to carbon based electrode materials [6].

Many electrochemical techniques make use of the reduction of $H_2O_2$ by the catalysis of immobilized horseradish peroxidase (HRP) to construct unmediated HRP-based sensors, which are based on direct electron transfer between an electrode and immobilized HRP [8-12]. It has been reported that proteins containing heme groups, such as hemoglobin, and myoglobin possess peroxidase like catalytic activity, which can reduce $H_2O_2$ due to the electroactive heme center and has also been used for the preparation of $H_2O_2$ sensors [13-16].

Throughout this application, various patents and publications are referenced, and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive efforts to develop a high-throughput sensor for detecting hydrogen peroxide with higher sensitivity useful in the industrial field. As a result, the present inventors have found that where hydrogen peroxide is contacted to an electrode comprising gold nanoparticles and cytochrome c on a conducting oxide substrate, current values are increased depending on concentrations of hydrogen peroxide, thereby permitting to detect hydrogen peroxide in more rapid and convenient manner.

Accordingly, it is an object of this invention to provide the sensor for detecting hydrogen peroxide.

It is another object of this invention to provide the method for detecting hydrogen peroxide in analytical sample.

Other objects and advantages of the present invention will become apparent from the following detailed description together with the appended claims and drawings.

BRIEF DESCRIPTION OF THE DRAWINGS

FIG. 2, part (a) to FIG. 2, part (c), represent a bare ITO surface, AuNPs on ITO surface and cyt c immobilized ITO/AuNP electrode surface, respectively. Scale bar represents 500 nm. FIG. 2, part (d), represents the topographical image of ITO surface, scale bar 250 nm. FIG. 2, part (g), represents the roughness analysis of FIG. 2, part (d). FIG. 2, part (e), represents the topographical image of AuNPs adsorbed on ITO/MPTMS surface. FIG. 2, part (h), represents the roughness analysis of FIG. 2, part (e). FIG. 2, part (f), represents the topographical image of cyt c adsorbed on ITO/AuNP surface. FIG. 2, part (i), represents the roughness analysis of FIG. 2, part (f). Images were scanned at a rate of 1 Hz. $R_a$, Mean roughness; $R_q$, RMS; $R_{max}$, Max height; $R_z$, 10 pt mean; $R_p$, Max. peak height; $R_{pm}$, Avg. max. height; $R_{vm}$, Max. depth.

FIG. 4, part (a), represents cyclic voltammograms for (i) bare ITO, (ii) ITO/AuNP, (iii) ITO/AuNP/cyt c electrode in HEPES buffer solution at pH 7 at a scan rate of 0.05 $Vs^{-1}$.

FIG. 4, part (b), represents cyclic voltammograms of ITO/AuNP/cyt c electrode in 10 mM, pH 7.0, HEPES buffer with increasing scan rate from 0.01 to 0.1 $Vs^{-1}$.

FIG. 5, part (a), represents a plot of the cathodic ($i_{pa}$) peak currents vs. scan rate.

FIG. 5, part (b), represents a plot of the cathodic ($i_{pc}$) and anodic ($i_{pa}$) peak currents vs. log(scan rate)$^{1/2}$.

FIG. 5, part (c), represents a variation of peak potential ($E_{pa}$ and $E_{pc}$) vs. logarithm of scan rate of ITO/AuNP/cyt c electrode in 10 mM pH 7.0, HEPES buffer. Straight lines indicate the linear fit of the curves.

DETAILED DESCRIPTION OF THIS INVENTION

In an aspect of the present invention, there is provided a sensor for detecting hydrogen peroxide, comprising: (a) a gold (Au) nanoparticle conjugated with a conducting oxide substrate comprising a conductive oxide; (b) a cytochrome c (cyt c) immobilized on the gold nanoparticle.

The present inventors have made intensive efforts to develop a high-throughput sensor for detecting hydrogen peroxide with higher sensitivity useful in the industrial field. As a result, the present inventors have found that where hydrogen peroxide is contacted to an electrode comprising gold nanoparticles and cytochrome c on a conducting oxide substrate, current values are increased depending on concentrations of hydrogen peroxide, thereby permitting to detect hydrogen peroxide in more rapid and convenient manner.

One of the most prominent features of the present invention is to prepare a conducting oxide electrode by depositing conductive oxides on a glass substrate. The electrode may be formed on the surface of the substrate by various methods known in the art. Preferably, the method includes an electron beam evaporation, a vacuum evaporation, a thermal evaporation, a spin coating, a sputtering, a low pressure chemical vapor deposition, a sol-gel synthesis, an electrical plating and an electroless plating.

As used herein the term "conductive oxide" refers to a conducting film which is optically transparent and electrically conductive. The conducting film for photovoltaic applications may be fabricated from both inorganic and organic materials. The inorganic films typically are made up of general conductive oxide layers such as indium-tin oxide, fluorine doped thin oxide, and doped zinc oxide. The organic films are being developed using carbon nanotube networks and graphene, which can be fabricated to highly transparent to the infrared light, along with networks of polymers such as poly(3,4-ethylenedioxythiophene) and its derivatives. Most of these films are fabricated with polycrystalline or amorphous microstructures. On average, these applications use electrode materials that have greater than 80% transmittance of incident light as well as conductivities higher than $10^3$ S/cm for efficient carrier transport.

Preferably, the conductive oxide is selected from the group consisting of an indium-tin oxide, a indium-zinc oxide, a tin oxide, a zinc oxide, a copper-aluminum oxide, a copper-gallium oxide, a copper-scandium oxide, a copper-chrome oxide, a copper-indium oxide, a copper-yttrium oxide and a silver-indium oxide, more preferably, an indium-tin oxide (ITO).

Indium-tin oxide (ITO, or tin-doped indium oxide) used in the present invention is a solid material of indium (III) oxide ($In_2O_3$) and tin (IV) oxide ($SnO_2$), generally 90% $In_2O_3$ and 10% $SnO_2$ by weight. The indium-tin oxide shows low resistivity as electron concentration becomes increased due to electron generation in the replacement of $In^{3+}$ ions by $Sn^{4+}$ ions. As the replacement requires high energy, it is general knowledge to one of skill in the art that indium-tin oxide electrodes with low resistivity may be fabricated by heating a glass substrate over 300° C. to easily replace indium ions by tin ions. ITO is transparent and colorless in thin layers while in bulk form it is yellow to grey. In the infrared region of the spectrum it acts as a metal-like mirror.

Indium-tin oxide is one of the most widely used transparent conductive oxides because of its electrical conductivity and optical transparency, as well as the ease with which it can be deposited as a thin film. As, with all transparent conducting films, a compromise must be made between conductivity and transparency, since increasing the thickness and increasing the concentration of charge carriers will increase the material's conductivity, but decrease its transparency.

The ITO films are most commonly deposited on surfaces by an electron beam evaporation, a physical vapor deposition, or a range of sputter deposition techniques.

Another feature of the present invention is to immobilize gold nanoparticles onto the surface of the conducting oxide substrate.

Preferably, the gold nanoparticle is indirectly conjugated with the conducting oxide substrate through a sulfhydryl group introduced to the surface of the conducting oxide substrate.

According to a preferable embodiment of the present invention, the ITO substrate on a glass plate is incubated overnight in methanol containing 3-MPTMS (3-Mercaptopropyl trimethoxysilane) to generate —SH groups on the ITO surface. After washing, ITO/AuNP hybrid is prepared by immersing the ITO/MPTMS substrate in the gold colloidal solution for 2 hr, which produced the ITO/AuNP substrate through metal-thiol interactions.

Another feature of the present invention is immobilization of cytochrome c (cyt c) on the conducting oxide/AuNP hybrid.

According to a preferable embodiment of the present invention, the ITO/AuNP electrode is incubated with 30 mM 11-MUA (11-mercaptoundecanoic acid) and then activated with EDC(N-ethyl-N'-(3-(dimethylamino)propyl)carbodiimide) and NHS (N-hydroxysuccinimide). The ITO/AuNP/cyt c electrode is prepared by adding 20 μl of cyt c to the activated electrode surface and washed with distilled water to remove any unbound protein molecules, followed by drying under a $N_2$ stream.

Because cytochrome c has a unique peroxidase activity and is not a oxygen-specific protein, it is not interfered with the presence of oxygen under applied voltage. The heme prosthetic group of cytochrome c is very unlikely to be lost in reactions in organic solvents, because it is covalently linked to the protein. Since cytochrome c is active over a wide range of pH from pH 2 to pH 11 and shows excellent thermo stability, it is able to perform biocatalytic reactions even at higher temperatures and after chemical modification. Furthermore, cytochrome c is economical in bulk biocatalysis due to its inexpensive price.

Preferably, cytochrome c is indirectly immobilized on the gold nanoparticle through an amino group introduced to the surface of the gold nanoparticle.

The electrochemical performance of the present sensor for detecting hydrogen peroxide will be described as follows:

The present invention relates to a sensor device for electrochemically detecting hydrogen peroxide by changing the oxidation and reduction state of immobilized proteins depending on the concentration of hydrogen peroxide. The substrate having the protein layer is incubated in an electrolyte solution, e.g. a HEPES electrolyte. The substrate is operated by connecting to a potentiostat as a working electrode, and a reference electrode (e.g., Ag/AgCl) and a counter electrode (e.g., Pt) are incorporated into the electrolyte. The reference electrode is a reference to read the potential changes of the working electrode in the potentiostat during voltage sweep. The counter electrode is a passage of electrons flowing as a result of the control of potential by the potentiostat. Such a three-electrode system is one of the most commonly used systems in the field of electrochemistry. In the simple electrochemical system described above, a voltage-current curve is obtained using the cyclic voltammetry method. An open-circuit potential is measured to investigate the equilibrium potential of the electrochemical system constructed. The open-circuit potential refers to a potential difference formed due to the intrinsic property of the protein layer and the electrolyte in a voltage-free state, i.e. in a circuit-broken state, naturally reaching equilibrium in the constructed system. Based on the above principle, a system can be artificially made close to the equilibrium state by applying an open-circuit potential to the system if the open-circuit potential is known. To describe in more detail, after the protein is reduced by accepting electrons from the electrolyte as the reduction potential is applied to the protein layer, electrons are released while the protein returns to the equilibrium state as the open-circuit potential is applied. Conversely, after the protein is oxidized by releasing the electrons, it returns to the original potential state by accepting electrons when the open-circuit potential is applied. Therefore, the open-circuit potential allows to read the redox state of the protein layer.

Preferably, the sensor further comprises a counter electrode and a reference electrode.

The hydrogen peroxide-detecting sensor of this invention is capable of detecting hydrogen peroxide with higher sensitivity, preferably with a detection limit of 0.3-0.8 µM, more preferably 0.4-0.6 µM, still more preferably 0.5 µM. The present sensor is capable of reaching to a steady-state current in less than 10 sec, allowing to rapidly obtain detection results.

In another aspect of this invention, there is provided a method for detecting hydrogen oxide in a sample, comprising:

(a) preparing the sensor of the present invention described above;
(b) contacting the sample with the sensor; and
(c) measuring an electrical signal generated in the step (b).

The term used herein "sample" includes, but not limited to, biological samples (e.g., tissues, cells, a body fluid, blood, plasma and serum) and environmental samples.

The detection of hydrogen peroxide by the conductive oxide/AuNP/cyt c electrode can be described with the following reaction scheme:

Cytochrome-Fe(II) is produced by electron release from cytochrome-Fe(III). Two molecules of cytochrome-Fe(II) and 2H$^+$ plus H$_2$O$_2$ are then reacted to generate two molecules of cytochrome-Fe(III) and two water molecules in which hydrogen peroxide undergoes reduction to increase current values, thereby detecting the concentration of hydrogen peroxide.

The features and advantages of the present invention will be summarized as follows:

(a) The present invention provides a high-throughput sensor capable of detecting hydrogen peroxide with much higher sensitivity.

(b) Cytochrome c used in the present sensor is not interfered with oxygen unlike to hemoglobin and myoglobin conventionally used in hydrogen peroxide sensors. In addition, cytochrome c is active over a wide range of pH from pH 2 to pH 11 and shows excellent thermo stability. Therefore, cytochrome c is capable of performing biocatalytic reactions at high temperatures and after chemical modification.

(c) In the performance of the present sensor, current values are increased in parallel with increased hydrogen peroxide concentration. Such performance enables to easily analyze the presence or concentration of hydrogen peroxide.

The present invention will now be described in further detail by examples. It would be obvious to those skilled in the art that these examples are intended to be more concretely illustrative and the scope of the present invention as set forth in the appended claims is not limited to or by the examples.

EXAMPLES

Experimental Materials and Experimental Methods

1. Chemical Reagents

Cytochrome c (cyt c) from horse heart was purchased from Sigma-Aldrich, purity 99.7% based on H$_2$O content 7.0%) and used as received without further purification. 3-Aminopropyl triethoxysilane (3-APTES; purity: 99%), 3-Mercaptopropyl trimethoxysilane (3-MPTMS; purity: 85%) and gold colloid solution (~0.01% HAuCl$_4$) were purchased from Sigma-Aldrich. Glutaraldehyde solution, 11-mercaptoundecanoic acid (MUA, Aldrich) were purchased from Sigma and used as received without any further purification. N-hydroxysuccinimide (NHS), 1-ethyl-3-(3-diethylaminopropyl) carbodiimide hydrochloride (EDC) was obtained from Sigma. 30% hydrogen peroxide was brought from Daejung Materials and Chemicals, Korea and diluted in DI water to prepare molar solutions. 10 mM HEPES buffer solution (pH 7.0) was used in all electrochemical experiments. All solutions were prepared with water (18 MΩcm) that was purified using a Milli-Q system (Millipore, Bedford, Mass.).

2. Electrode Modification

Indium-tin oxide [ITO; 20 Ω/cm$^2$] with a thickness of 400 nm were used in these experiments. The transparent electrodes were cleaned by ultrasonic cleaning in successive solutions of Triton X-100/water (1:5, v/v), water, and ethanol for at least 40 min each. The ITO electrode was then heated in a 1:1:5 solution of NH$_4$OH:H$_2$O$_2$:H$_2$O for 40 min at 80° C., rinsed thoroughly with water, and dried under a stream of nitrogen gas to generate —OH groups on the surface [21].

3. Formation of Nanoparticles and Cytochrome c Hybrid on ITO Surface

For the formation of AuNP-cyt c hybrid, the —OH.terminated ITO substrates were incubated with 2% (v/v) 3-MPTMS in methanol overnight to generate —SH groups on the ITO surface. After rinsing thoroughly, the ITO/MPTMS substrates were immersed in the gold colloidal solution for 2 hr, which produced the ITO/AuNPs substrate through metal-thiol interactions. For the construction of ITO/AuNPs/cyt c substrate, the ITO/AuNPs were incubated with 30 mM 11-MUA and activated with EDC and NHS. 20 µl of cyt c was then added to the activated electrode surface. The ITO/AuNP/cyt c were slightly washed with DI water to remove any unbound protein molecules and dried under a N$_2$ stream.

Figure 1:
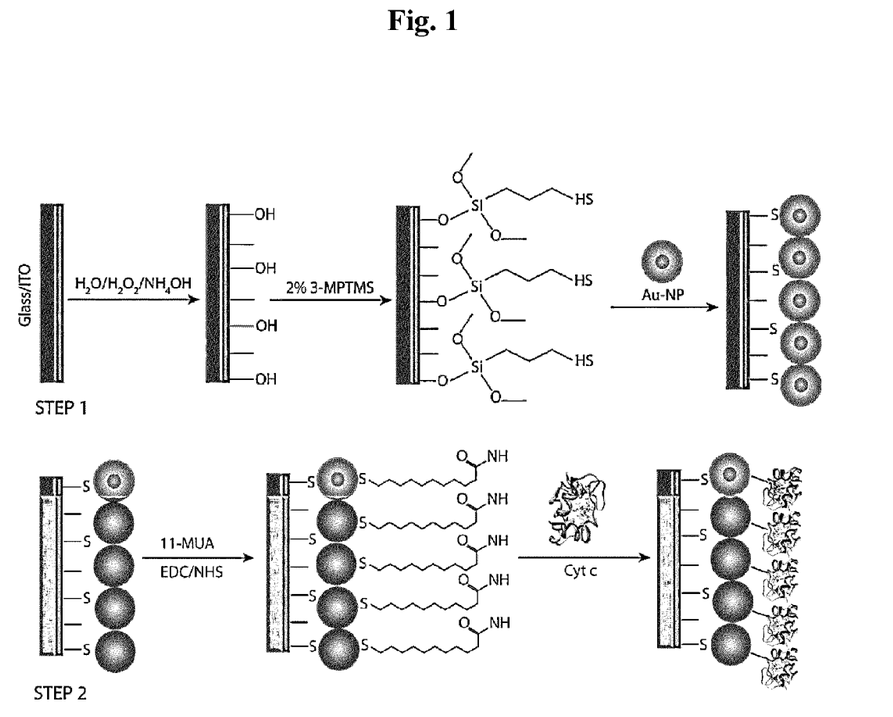
FIG. 1 represents the schematization of an electrode modification process for immobilizing cytochrome c (cyt c) on an indium-tin oxide (ITO)/gold nanoparticle (AuNP) electrode.

For the preparation of cyt c/ITO electrodes, ITO electrodes were incubated with a 2% APTES solution in ethanol for 6 hr. The samples were then washed with ethanol and DI water. Subsequently the substrates were immersed into 1% glutaric anhydride (GA) overnight at room temperature. The functionalized substrates were washed with DI water and then dried under a N$_2$ stream. 20 µl cyt c was then incubated on the substrate for 3 hr and slightly washed with DI water and dried under a N$_2$ stream. The electrode modification processes for cyt c immobilization on the ITO/AuNP electrode is represented in the schematic diagram of FIG. 1.

4. Characterization of ITO/AuNP/Cyt c Surface

Surface topography of the bare ITO, ITO/AuNP and ITO/AuNP/cyt c electrode surfaces was investigated by atomic force microscopy (AFM) (Nanoscope IV/Multimode, Digital Instruments). All images were recorded in tapping mode using silicon cantilevers with a resonance frequency ($f_o$) between 250 and 300 kHz. All images were measured in air at a temperature of 22° C. The roughness and sectional analysis of the images were performed using the offline procedure provided by Nanoscope (Nanoscope IV/Multimode, Digital Instruments). The SEM measurements were performed using a JEOL JSM S-4300 at an operating voltage of 20 kV.

A set of roughness parameters have been developed for versatile characterization of the three electrode surface properties. The root mean square (RMS) roughness $R_q$ is the most widely used amplitude roughness parameter, which gives the standard deviation of height. Amplitude parameters $R_z$ gives the extreme height deference for an image. The surface skewness $R_{sk}$ describes the asymmetry of the height distribution. A skewness value of zero represents a Gaussian-like surface.

Negative values of $R_{sk}$ refer to a surface-porous sample, where the valleys dominate the peaks and positive $R_{sk}$ values indicate that the local summits dominate the valleys.

The X-ray diffraction patterns of the prepared samples were recorded with Cu Kα radiation (λ) 1.54056 Å of a Rigaku X-ray diffractometer at a scanning rate of 0.02° per second in 2θ. The X-ray diffractometer was operated at 40 kV and 150 mA.

5. Electrochemical Activity and Detection of $H_2O_2$

Cyclic voltammetry (CV) was performed with a three-electrode system using the ITO/AuNP/cyt c substrate as the working electrode, platinum coil as the counter electrode, and Ag/AgCl/KCl$_{sat}$ as the reference electrode. Experiments were performed using a CHI 660A potentiostat equipped with general purpose electrochemical software and operated in a potential range from 0.2 to −0.4 V at a scan rate 50 mVs$^{-1}$. The DPV and chronoamperometric experiments were performed using the ITO/AuNP/cyt c modified ITO electrodes with various concentrations of $H_2O_2$. The potential was set at −0.10 V and the current-time curves were recorded after successive additions of 20 μl aliquots of 200 mM $H_2O_2$ in 5 ml of 10 mM HEPES, pH 7.0.

Results and Discussion

1. Topographic Analysis Using SEM and AFM

Figure 2:
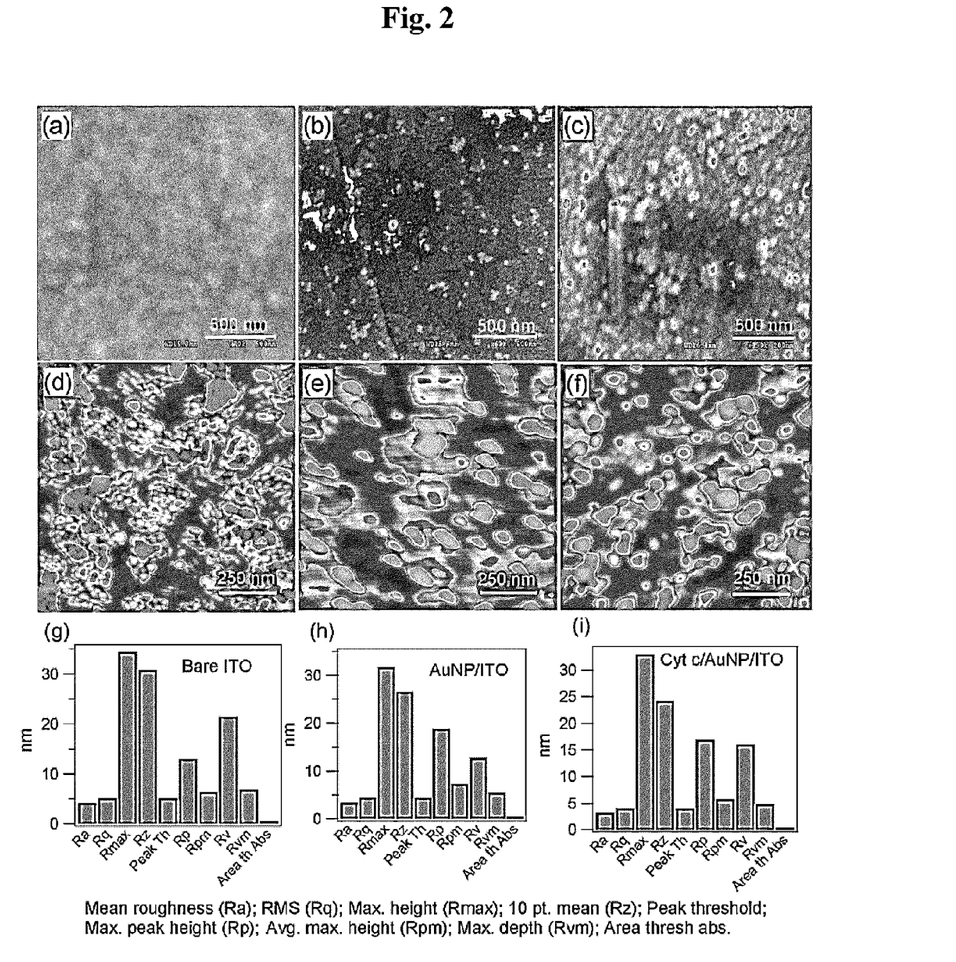
FIG. 2 represents the SEM images.

The topographical features of the ITO, ITO/AuNP and ITO/AuNP/cyt c surfaces were examined by SEM (FIG. 2a-c). As shown in FIG. 2b, the AuNP was well attached on to the ITO surface and had a particle diameter of ~40 nm. In addition, the particles in FIG. 2c, which shows images of the particles after cyt c immobilization, had a larger diameter (~50 nm), confirming that the cyt c was attached to the AuNP on the ITO surface. FIG. 2d-f shows typical AFM images of three different (ITO, ITO/AuNP and ITO/AuNP/cyt c) sample surfaces scanned at a rate of 1 Hz. The sizes of AuNPs immobilized on the MPTMS/ITO were two to three times larger than those of the AuNPs colloids. This was due to the aggregation of AuNPs and the well-known convolution of the AFM tip. However, the images clearly show that cyt c was conjugated to the AuNPs on the ITO substrates. The roughness parameters obtained from the scanned images were shown in FIG. 2g-i and the selected roughness parameters of the three surfaces are given in Table 1.

TABLE 1

Values of selected roughness parameters measured from the surface analysis of AFM topography images for ITO, ITO/AuNP and ITO/AuNP/cyt c, respectively.

| | ITO surface | ITO/AuNP | ITO/AuNP/cyt c |
|---|---|---|---|
| Roughness average ($R_a$) (nm) | 4.20 ± 0.365 | 3.35 ± 0.75 | 3.19 ± 1.09 |
| RMS roughness ($R_q$) (nm) | 5.08 ± 0.386 | 4.40 ± 0.8 | 4.01 ± 1.04 |
| Peak to peak height ($R_t$) (nm) | 32.3 ± 3.31 | 45.1 ± 3.2 | 147 ± 11.73 |
| Skewness ($R_{sk}$) | −0.36 ± 0.11 | 0.56 ± 0.3 | 0.25 ± 0.16 |
| Kurtosis ($R_{ku}$) | 2.60 ± 0.314 | 3.13 ± 0.41 | 3.73 ± 0.433 |
| Max. peak height ($R_p$) (nm) | 12.9 ± 0.87 | 16.8 ± 4.08 | 18.8 ± 2.01 |
| Particle height (section analysis) (nm) | 3.48 ± 0.74 | 4.05 ± 0.57 | 15.0 ± 1.89 |

Using the offline sectional analysis provided by Nanoscope (Digital Instruments), the height of the AuNP and cyt c was found to be 4 nm and 15 nm, respectively, while the bare ITO contained large clusters of particles. The observed diameter of the AuNP particles was 40 nm, which indicates that these structures were aggregates of ~2 particles. Further, the size of a single cyt c molecule is 3 nm [22]; which means that aggregated AuNPs had attached to the ITO substrate, resulting in the formation of an AuNP-cyt c hybrid with an average diameter of ~50 nm. From Table 1, it is clear that the RMS roughness decreased for each sample and was higher for the bare ITO surface. This was expected since the ITO surface is rough and contains many grains with average diameters between 10 and 50 nm separated by deep valleys. In addition, based on the skewness ($R_{sk}$) values, it is clear that the peaks dominate the valleys. These combined results confirm that the particles (AuNPs and cyt c) were well immobilized on the surface. In addition, the kurtosis ($R_{ku}$) increased for all the samples, which further demonstrates that the high areas dominated over the valleys. Furthermore, the max. peak height ($R_p$) increased in all the three samples. Based on these results, it can be concluded that the cyt c was well attached to the AuNPs through LBL assembly, resulting in the formation of a hybrid (ITO/AuNP/cyt c) on the ITO surface.

Figure 3:
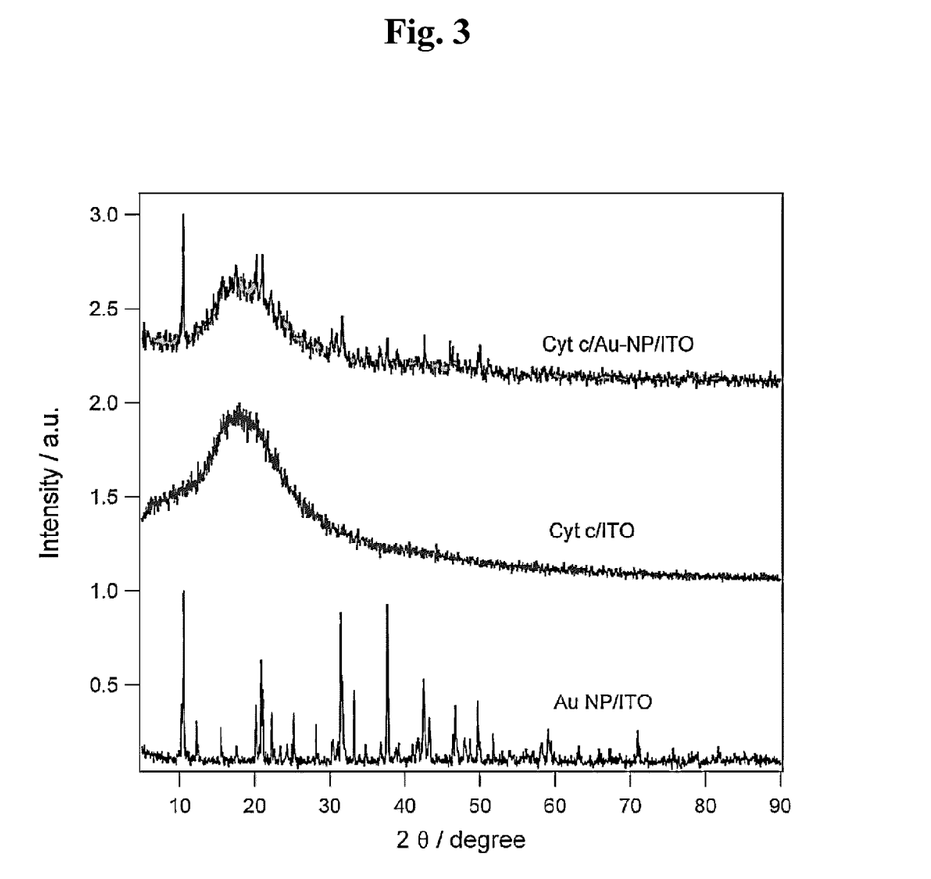
FIG. 3 represents X-ray diffraction patterns of (a) AuNP/ITO; (b) cyt c/ITO, (c) cyt c/AuNP/ITO surface, respectively.

2. X-Ray Diffraction Analysis for Confirming the Formation of Hybrid on ITO Electrode Experimental X-ray diffraction patterns were obtained for AuNPs, cyt c and AuNPs conjugated with cyt c as shown in FIG. 3. The XRD measurement was used mainly to confirm successful conjugation of cyt c to the AuNPs. As shown in FIG. 3, a typical pattern for AuNPs [spectrum (a)] was observed and the structure was confirmed based on the Joint Committee on Powder Diffraction Standards (JCPDS) Card file No. 01-073-1234. This pattern confirmed the cryrstallanity of the particles. In spectrum (b), a broad peak around 2θ=18 was observed due the Fe heme center of cyt c. In the XRD spectrum (c), diffraction peaks can be seen for both the nanoparticles along with a broad peak of cyt c. The spectrum of the AuNPs-cyt c conjugate showed a combination of these peaks, which proves that the layer-by-layer assembly process resulted in the formation of a hybrid system on the electrode surface.

3. Cyclic Voltammetric Behavior of ITO/AuNP/Cyt C electrode

Figure 4:
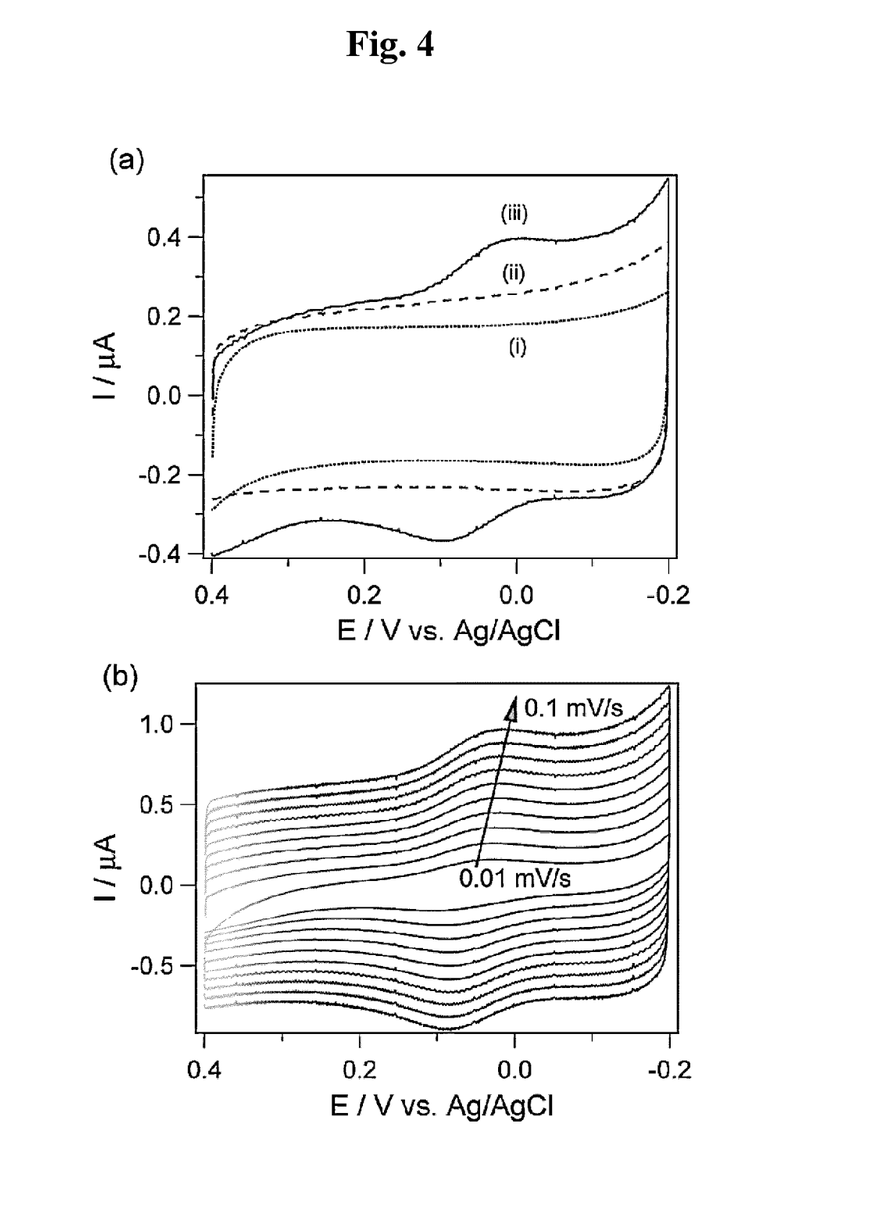

The cyclic voltammetric studies were carried out to examine the redox behavior of the ITO/AuNP/cyt c electrode in 10 mM pH HEPES buffer at a scan rate of 50 mV s$^{-1}$. As depicted in FIG. 4a, no obvious redox peaks were observed for both the electrodes, [ITO (curve i) and ITO/AuNP electrodes (curve ii)] in the potential range of 0.4 to −0.2 V. However, a small increase in the background current was observed for the ITO/AuNP electrode compared to the bare ITO electrode. Furthermore, the ITO/AuNP/cyt c electrode showed a couple of well-defined and quasi-reversible redox peaks (curve iii) because of the $Fe^{3+/2+}$ redox center, which was responsible for electron exchange. The anodic peak potential ($E_{pa}$) and cathodic peak potential ($E_{pc}$) were located at 0.09 and 0.02 V (vs. Ag/AgCl) respectively, with a peak-to-peak separation ($\Delta E_p$) of 70 mV. Moreover, the nanoparticles significantly enhanced the interfacial electrochemical electron transfer rate despite the increase in total distance between the redox center and the electrode surface.

Cyclic voltammograms of the ITO/AuNP/cyt c electrode in 10 mM pH 7.0 HEPES at different scan rates from 0.01 to 0.1 Vs$^{-1}$ were collected and are shown in FIG. 4b. All scan rates resulted in well-defined enhanced reduction and oxidation peaks with a slight shift in both cathodic and anodic peak potentials at different scan rates.

Figure 5:
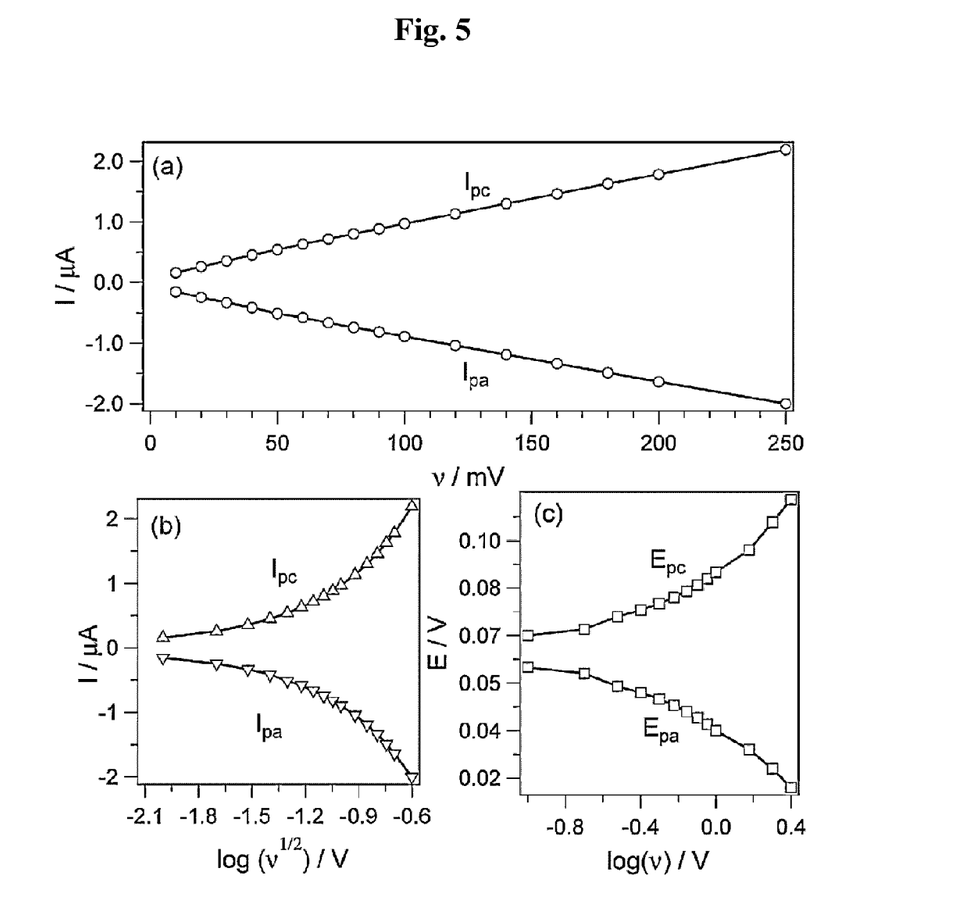

Furthermore, investigations on the ITO/AuNP/cyt c electrode revealed a linear plot for cathodic and anodic peak currents against the scan rate and logarithm of the scan rate as shown in FIG. 5a-b, respectively. Based on this analysis, an increase in scan rate resulted in a shift of the oxidation wave to a more positive potential, while the reduction wave shifted to a more negative potential. The anodic and cathodic peak potentials were linearly dependent on log u. A graph of $E_p$=f (log u) yielded two straightlines with a slope equal to $-2.3$ $RT/\alpha nF$ for the cathodic peak, and a slope of $2.3 RT/(1-\alpha)nF$ for the anodic peak, as shown in FIG. 5c. The chargetransfer coefficient ($\alpha$) value was determined to be 0.456 from the slope of the straight lines based on the following equation:

$$\log \frac{ka}{kc} = \log\left[\frac{a}{(1-a)}\right] \text{ or } \frac{ka}{kc} = \frac{a}{1-a} \quad (1)$$

Where ka (0.037) is the slope of the line derived from $E_{pa}$=f(log u); $k_c$ (0.044) is the slope of the line derived from; $E_{pc}$=f(log u); $\alpha$ is the charge-transfer coefficient. The apparent electron-transfer rate constant ($k_s$) for electron transfer between the electrode and the surface deposited layers was also to be 0.69 s$^{-1}$ according to the following equation [19];

$$\log ks = a\log(1-a) + (1-a)\log a - \log\left(\frac{RT}{nFu}\right) - \frac{a(1-a)nF\Delta Ep}{2.3RT} \quad (2)$$

Furthermore, the surface concentration ($\Gamma$) of the cyt c molecules on the ITO/AuNP/cyt c electrode could be estimated based on the slope of Ip vs. using the following equation:

$$I_p = \frac{n^2 F^2 A \Gamma u}{4RT} \quad (3)$$

Where $I_p$ is the reduction peak current, u is the scan rate and A is the electrode surface area, respectively. F is the Faraday constant, R is the gas constant and T is the absolute temperature. The value of $\Gamma$ was calculated to be 4.2 10.10 mol/cm$^{-2}$.

4. Electrocatalytic Reduction of $H_2O_2$ at the Modified Electrode

Figure 6:
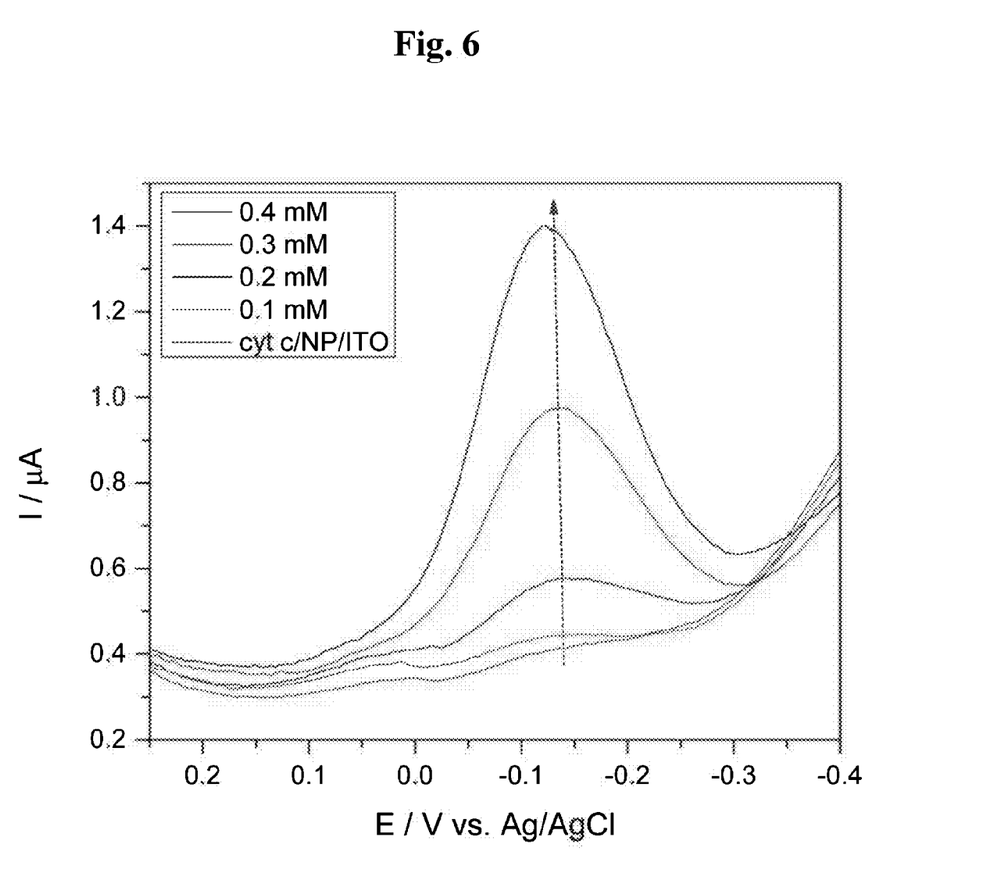
FIG. 6 represents a differential pulse voltammetry of the ITO/AuNP/cyt c electrode as a function of $H_2O_2$ upon successive additions of 5 µl aliquots of 100 mM $H_2O_2$ in 5 ml solution of 10 mM HEPES buffer at pH 7. The features indicated in the box (0.4 mM etc.) correspond to the respective curves from the top down at the point of the vertical arrow.

Differential pulse voltammetry technique has the ability to determine the highest sensitivity and the lowest detection limit of any electrochemical sensor. Hence, the electrochemical response of the ITO/AuNP/cyt c electrode was observed as a function of $H_2O_2$ concentration. FIG. 6 shows the differential pulse voltammogram in a buffer solution of 10 mM HEPES (pH 7.0), which clearly shows a well-defined higher differential pulse peak for the $H_2O_2$ catalytic reduction current at $-0.1$ V. The potential of $-0.1$ V was selected because the complete reduction of cyt c occurs at $-0.1$ V even though the reduction starts at 0.02 V. The current response increased when the $H_2O_2$ concentration was increased from 0.1 mM to 0.4 mM. The magnitude of the current also increased linearly upon the addition of several concentrations of $H_2O_2$. Thus, these results clearly demonstrate that by using the differential pulse technique, the modified electrode can be used as for the accurate and sensitive detection of $H_2O_2$.

5. Amperometric Determination of $H_2O_2$ at the Modified Cyt c/AuNP/ITO Electrode Cyt c possesses intrinsic peroxidase activity due to its similarity with peroxidase for catalysis of $H_2O_2$ [20]. The electrocatalytic response of the ITO/AuNP/cyt c to $H_2O_2$ was investigated and the principle of catalyzing $H_2O_2$ can be described using the following equation.

$$cyt\ c\text{-Fe(III)} + e^- \to cyt\ c\text{-Fe(II)} \quad (4)$$

$$2cyt\ c\text{-Fe(II)} + 2H^+ + H_2O_2 \to 2cyt\ c\text{-Fe(III)} + 2H_2O \quad (5)$$

Figure 7A:
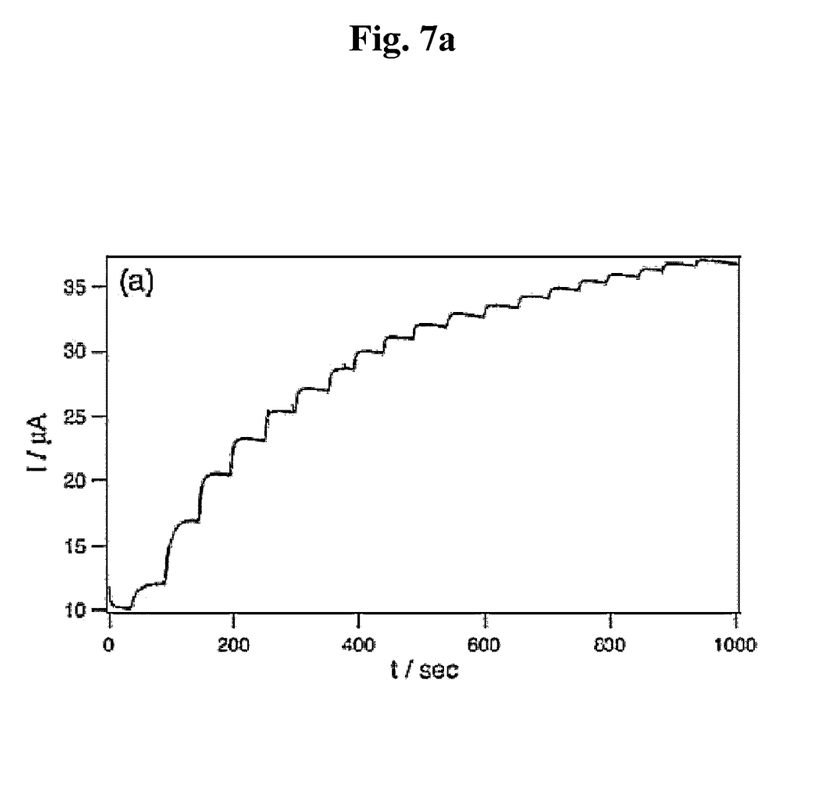
FIG. 7a represents a current-time curve obtained for ITO/AuNP/cyt c electrode upon successive additional of 20 µl aliquots of 200 mM $H_2O_2$ to 5 ml stirred 10 mM HEPES buffer at pH 7 with an applied potential of −0.1 V under nitrogen atmosphere.
Figure 7B:
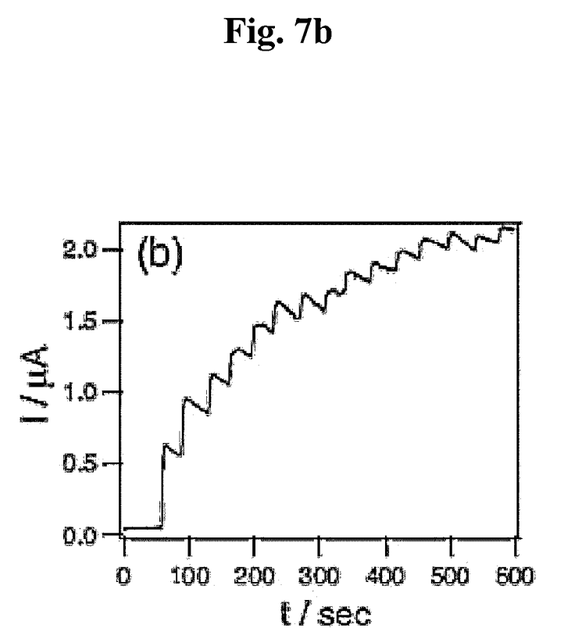
FIG. 7b represents a chronoamperometric curve obtained for cyt c/ITO.

The chronoamperometric experiment on the ITO/AuNP/cyt c electrode was carried out to measure the catalytic response of the hybrid molecules for $H_2O_2$ detection. FIG. 7a illustrates a typical current-time plot for the ITO/AuNP/cyt c on successive additions of 20 L aliquots of 200 mM $H_2O_2$ in 5 ml of 10 mM HEPES at pH 7. When an aliquot of $H_2O_2$ was added to the buffer solution, where the working electrode potential was set at 0.0.1 V, the reduction current increased steeply and then reached a stable value and this response was observed for every addition over a long period. As shown in FIG. 7b, a chronoamperometric curve was obtained for the cyt c/ITO electrode after the addition of 20 L aliquots of 200 mM $H_2O_2$ in 5 ml of 10 mM HEPES at pH 7. However, the addition of $H_2O_2$ resulted in only a slight increase in the current and the response was not as stable as compared with the AuNP/cyt c electrode. In addition, saturation was quickly reached when this system was used.

Figure 7C:
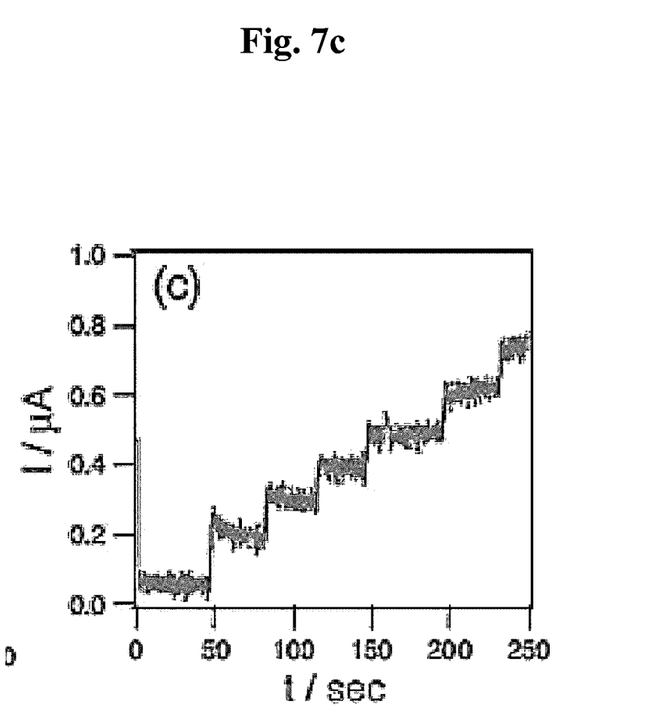
FIG. 7c represents AuNP/ITO obtained by the addition of 20 µl aliquots of 200 mM H2O2 in 5 ml stirred solution of 10 mM HEPES buffer at the potential of −0.1 V under nitrogen atmosphere.

FIG. 7c shows the amperometric curve for the ITO/AuNP in the absence of cyt c. When this system was used, the addition $H_2O_2$ only resulted in a slight increase in the current but the response quickly saturated. Overall, the developed electrode sensor showed a linear response to $H_2O_2$ concentration upto 6 mM. The current response vs. $H_2O_2$ concentration shows a linear increase in the reduction current. The detection limit of the present electrode sensor was 0.5 μM, which was comparable to other electrodes in terms of detection limit. In addition, due to the incorporation of AuNP, the electrode achieved a faster electron transfer rate. Table 2 summarizes the detection limit of the present electrode compared with previous studies. Furthermore, this system reached 95% of the steady-state current in less than 10 sec after the addition of $H_2O_2$. Thus, the electrode developed in this study showed a fast response for the detection of $H_2O_2$.

Conclusions

In conclusion, ITO/AuNP/cyt c was fabricated and used as an electrode for direct electrochemistry of cyt c by forming a hybrid to detect $H_2O_2$. The surface morphologies and the roughness parameters were investigated by AFM. The electrochemical properties of the ITO/AuNP/cyt c were characterized by using CV and other electrochemical methods. ITO/AuNP/cyt c displayed good redox behavior with enhanced peak currents due to the incorporation of AuNPs. Moreover, ITO/AuNP/cyt c displayed a good response in the electrocatalytic reduction of $H_2O_2$. Thus, the hybrid system with nanometer-sized AuNPs achieved direct electron transfer of cyt c, which allowed for the construction of an efficient biosensor for the detection of $H_2O_2$.

REFERENCES

[1] P. N. Bartlett, P. R. Birkin, J. H. Wang, F. Palmisano, G. D. Benedetto, *Anal. Chem.* 70 (1998) 3685.
[2] J. Wang, Y. Lin, L. Chen, *Analyst* 118 (1993) 277.
[3] T. T. Gu, Y. Hasebe, *Biosens. Bioelectron.* 21 (2006) 2121.
[4] S. Chen, R. Yuan, Y. Chaff, L. Zhang, N. Wang, X. Li, *Biosens. Bioelectron.* 22 (2007) 1268.
[5] D. Du, J. Ding, J. Cai, A. Zhang, *Colloids Surf. B* 58 (2007) 145.
[6] F. Gao, R. Yuan, Y. Chaff, S. Chen, S. Cao, M. Tang, *J. Biochem. Biophys. Methods* 70 (2007) 407.

[7] H. Qi, C. Zhang, X. Li, *Sens. Actuators B* 114 (2006) 364.
[8] J. Jia, B. Wang, A. Wu, G. Cheng, Z. Li, S. Dong, *Anal. Chem.* 74 (2002) 2217.
[9] A. Lindgren, T. Ruzgas, L. Gorton, E. Csoregi, G. B. Ardila, I. Y. Sakharov, I. G. Gazaryan, *Biosens. Bioelectron.* 15 (2000) 491.
[10] B.-H. Liu, F. Yan, J.-L. Kong, J.-Q. Deng, *Anal. Chim. Acta* 386 (1999) 31.
[11] E. E. Ferapontova, V. G. Grigorenko, A. M. Egorov, T. Borchers, T. Ruzgas, L. Gorton, *Biosens. Bioelectron.* 16 (2001) 147.
[12] S. Q. Liu, H. X. Ju, *Anal. Biochem.* 307 (2002) 110.
[13] H. Y. Gu, A. M. Yu, H. Y. Chen, *J. Electroanal. Chem.* 516 (2001) 119.
[14] S. Liu, Z. Dai, H. Chen, H. Ju, *Biosens. Bioelectron.* 19 (2004) 963.
[15] J.-J. Feng, G. Zhao, J.-J. Xu, H.-Y. Chen, *Anal. Biochem* 342 (2005) 280.
[16] L. Chen, G. Lu, *J. Electroanal. Chem.* 597 (2006) 51.
[17] S. K. Arya, A. K. Prusty, S. P. Singh, P. R. Solanki, M. K. Pandey, M. Datta, B. D. Malhotra, *Anal. Biochem.* 363 (2007) 210.
[18] M. Zhang, Y. Wu, X. Feng, X. He, L. Chen, Y. Zhang, *J. Mater. Chem.* 20 (2010) 5835.
[19] E. Laviron, *J. Electroanal. Chem.* 101 (1979) 19.
[20] N. A. Belikova, Y. A. Vladimirov, A. N. Osipov, A. A. Kapralov, V. A. Tyurin, M. V. Potapovich, L. V. Basova, J. Peterson, I. V. Kurnikov, V. E. Kagan, *Biochemistry* 45 (2006) 4998.
[21] S. K. Arya, A. K. Prusty, S. P. Singh, P. R. Solanki, M. K. Pandey, M. Datta, B. D. Malhotra, *Anal. Biochem.* 363 (2007) 210.
[22] M. Zhang, Y. Wu, X. Feng, X. He, L. Chen, Y. Zhang, *J. Master. Chem.* 141 (2009) 518.

What is claimed is:

1. An electrochemical sensor for detecting hydrogen peroxide, comprising: (a) a gold (Au) nanoparticle conjugated with a conducting oxide substrate comprising a conduction oxide; (b) a cytochrome c immobilized on the gold nanoparticle via a linker molecule of 11-mercaptoundecanoic acid (11-MUA); wherein (i) the 11-MUA is covalently bound to the surface of the gold nanoparticle through a thiol group and the cytochrome c is covalently linked to the surface of the gold nanoparticle via an amide bond formed between a carboxylic group of the 11-MUA and an amino group of the cytochrome c, and (ii) the detection limit of the sensor for hydrogen peroxide is 0.3-0.8 μM and the sensor reaches a steady-state current in less than 10 sec.

2. The electrochemical sensor according to claim 1, wherein the conducting oxide is selected from the group consisting of a indium-tin oxide, a indium-zinc oxide, a tin oxide, a zinc oxide, a copper-aluminum oxide, a copper-gallium oxide, a copper-scandium oxide, a copper-chrome oxide, a copper-indium oxide, a copper-yttrium oxide and a silver-indium oxide.

3. The electrochemical sensor according to claim 2, wherein the conducting oxide is the indium-tin oxide.

4. The electrochemical sensor according to claim 1, wherein the gold nanoparticle is indirectly conjugated with the conducting oxide substrate through a sulfhydryl group introduced to the surface of the conducting oxide substrate.

5. The electrochemical sensor according to claim 1, wherein the sensor further comprises a counter electrode and a reference electrode.

6. A method for detecting hydrogen peroxide electrochemically in a sample, comprising;
    (a) preparing the electrochemical sensor according to claim 1;
    (b) contacting the sample to the electrochemical sensor; and
    (c) measuring an electrical signal generated in the step (b).

* * * * *